(12) United States Patent
Bouleau et al.

(10) Patent No.: US 9,995,802 B2
(45) Date of Patent: Jun. 12, 2018

(54) VERY LOW TEMPERATURE NMR METHOD AND DEVICE

(71) Applicant: COMMISSARIAT A L'ENERGIE ATOMIQUE ET AUX ENERGIES ALTERNATIVES, Paris (FR)

(72) Inventors: Eric Bouleau, Sassenage (FR); Gaël De Paëpe, Voiron (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 896 days.

(21) Appl. No.: 14/364,853

(22) PCT Filed: Dec. 11, 2012

(86) PCT No.: PCT/EP2012/075088
§ 371 (c)(1),
(2) Date: Jun. 12, 2014

(87) PCT Pub. No.: WO2013/087626
PCT Pub. Date: Jun. 20, 2013

(65) Prior Publication Data
US 2015/0177341 A1    Jun. 25, 2015

(30) Foreign Application Priority Data
Dec. 13, 2011    (FR) ...................... 11 61510

(51) Int. Cl.
*G01V 3/00* (2006.01)
*G01R 33/31* (2006.01)
(Continued)

(52) U.S. Cl.
CPC ............ *G01R 33/31* (2013.01); *G01N 24/08* (2013.01); *G01R 33/305* (2013.01); *G01R 33/307* (2013.01)

(58) Field of Classification Search
CPC ...... G01R 33/31; G01R 24/08; G01R 33/305; G01R 33/307
(Continued)

(56) References Cited

U.S. PATENT DOCUMENTS 4,266,194 A * 5/1981 Hlavka .................. G01R 33/31
                                                324/315
4,456,882 A   6/1984 Doty
(Continued)

FOREIGN PATENT DOCUMENTS

EP    0 249 383 A2   12/1987
EP      0916890 A2    5/1999
(Continued)

OTHER PUBLICATIONS

EPO Office Action dated Apr. 1, 2016 issued in corresponding European application No. 12806404.5 (with English machine-translation; 10 pages).
(Continued)

*Primary Examiner* — Susan Lee
(74) *Attorney, Agent, or Firm* — Westerman, Hattori, Daniels & Adrian, LLP

(57) ABSTRACT

The NMR analysis method for analyzing a solid sample positioned in a sample-holder (21) includes generation of a plurality of high-pressure gaseous flows (2, 3, 4) from at least one first source (1) of a high-pressure gas; cooling of the gaseous flows (2, 3, 4) in at least one heat exchanger (12) from a coolant gas (15) originating from at least one second source (11) of gas; and rotation of the sample-holder (21) by a first cooled high-pressure gaseous flow (2) and cooling of the sample-holder by a second cooled high-pressure gaseous flow (3).

20 Claims, 4 Drawing Sheets

Figure 1:
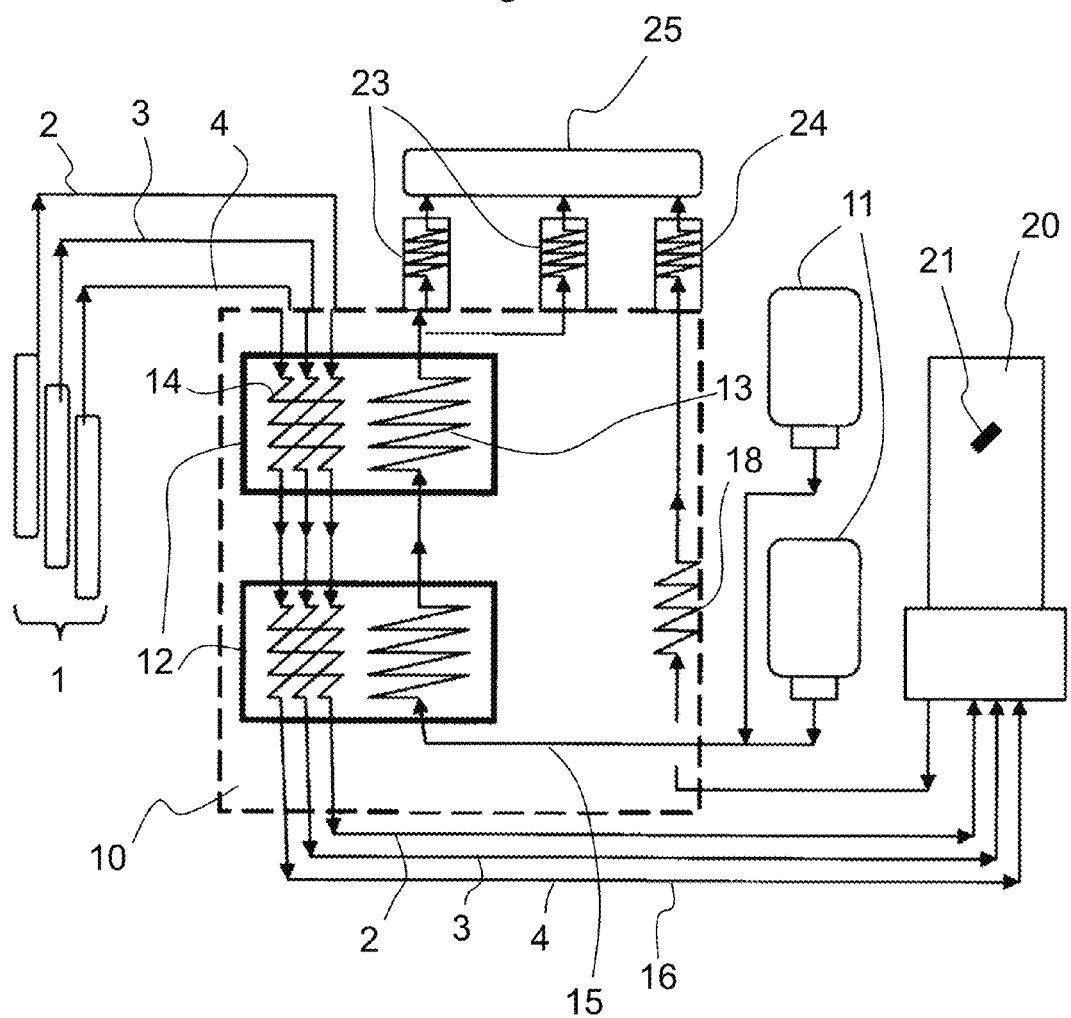

(51) Int. Cl.
*G01R 33/30* (2006.01)
*G01N 24/08* (2006.01)

(58) Field of Classification Search
USPC .......................................................... 324/309
See application file for complete search history.

(56) References Cited

U.S. PATENT DOCUMENTS

| | | | |
|---|---|---|---|
| 4,739,270 | A | 4/1988 | Daugaard et al. |
| 5,289,130 | A | 2/1994 | Doty |
| 5,410,286 | A * | 4/1995 | Herd ................. G01R 33/3815 335/216 |
| 5,960,636 | A | 10/1999 | Schuck et al. |
| 7,541,807 | B2 | 6/2009 | Stringer |
| 7,570,053 | B2 * | 8/2009 | Hasegawa .............. G01R 33/31 324/307 |
| 8,547,099 | B2 | 10/2013 | Takegoshi et al. |
| 8,683,816 | B2 * | 4/2014 | Krencker ............... G01R 33/31 165/164 |
| 2010/0321018 | A1 * | 12/2010 | Takegoshi .......... G01R 33/3403 324/318 |
| 2011/0080171 | A1 | 4/2011 | Takegoshi et al. |
| 2011/0284192 | A1 * | 11/2011 | Grossniklaus ......... G01R 33/31 165/135 |

FOREIGN PATENT DOCUMENTS

| | | |
|---|---|---|
| EP | 0916890 A3 | 7/2000 |
| EP | 2 306 215 A1 | 4/2011 |
| JP | 2007017391 A * | 1/2007 |

OTHER PUBLICATIONS

Barnes et al., "Cryogenic sample exchange NMR probe for magic angle spinning dynamic nuclear polarization", Journal of Magnetic Resonance, vol. 198, 2009, pp. 261-270; cited in the ISR.

D'Arco et al., "Velocity and pressure measurements for microturbine control in NMR application", Instrumentation and Technology Conference, May 1-3, 2007, pp. 1-5; cited in the ISR.

Mizuno et al., "Development of a magic-angle spinning nuclear magnetic resonance probe with a cryogenic detection system for sensitivity enhancement", Review of Scientific Instruments, vol. 79, 044706, 2008, pp. 1-6; cited in the ISR.

International Search Report dated Apr. 16, 2013 issued in corresponding application No. PCT/EP2012/075088.

* cited by examiner

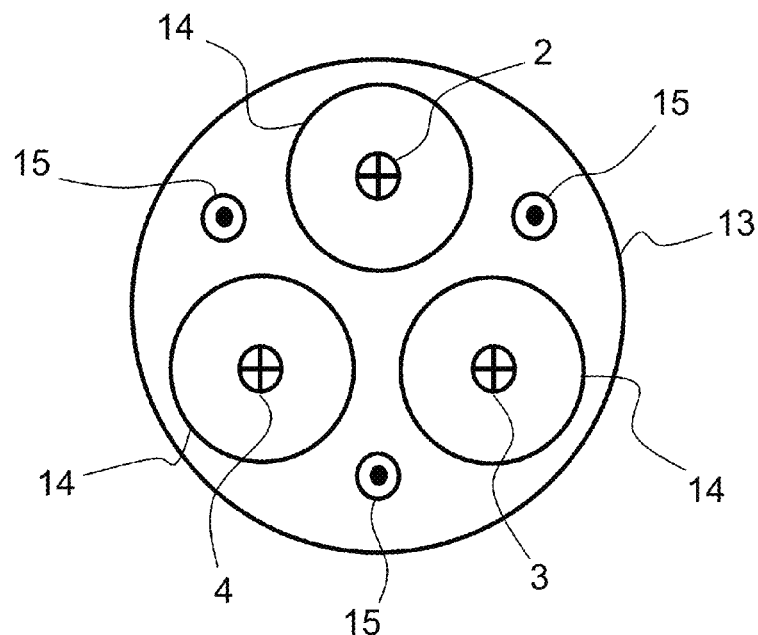
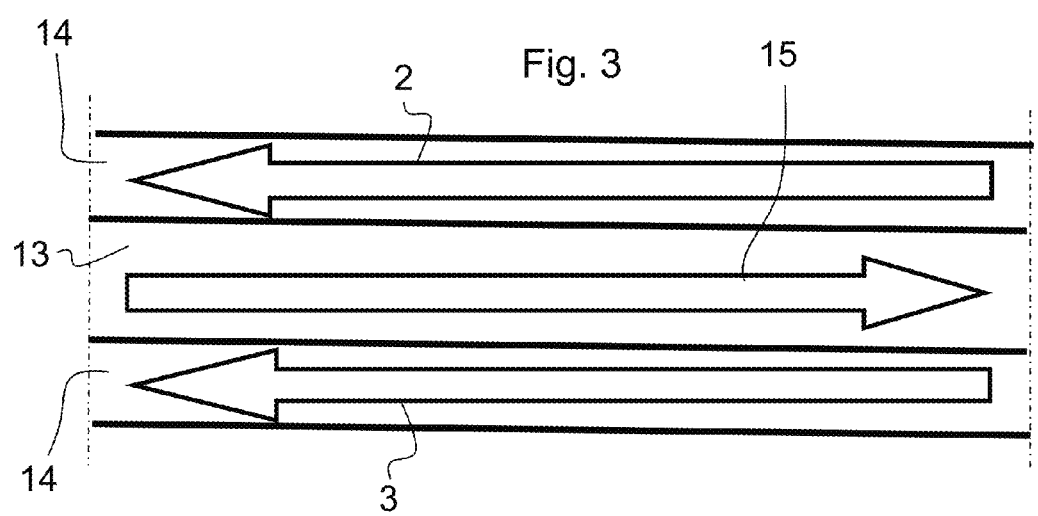

VERY LOW TEMPERATURE NMR METHOD AND DEVICE

The invention relates to a nuclear magnetic resonance (NMR) method and device that is particularly suitable for analysing a sample in the solid state.

An NMR device comprises a sample-holder rotated in a static magnetic field and exposed to a second magnetic field at right angles to the first and created by a radiofrequency coil, which in return receives a signal which is analysed to deduce from it information concerning a solid sample arranged in the sample-holder. According to one embodiment from the prior art, three gaseous flows originating from one and the same source, a standard container such as a helium cylinder at raised pressure, are directed towards the probe of the device which comprises the sample-holder. The function of the first flow is to rotate this sample-holder, by acting on blades or fins of a turbine driving a rotor which comprises the sample-holder. The function of the second flow is to bring the sample to a certain temperature, and the third flow creates a hydrostatic gas bearing supporting the rotor in the stator.

The search for better efficiency in analysing a sample in the solid state by NMR uses a rotation of the sample on a particular axis called "the magic angle". It is important to reach a high rotation speed. Also, the increase in the intensity of the magnetic fields, which currently reaches approximately 20 Tesla, has improved the sensitivity of the NMR detection. It is, however, very difficult these days to increase this intensity.

The existing solutions remain imperfect and inadequate and there is therefore a general need to improve the detection and analysis by NMR of a solid sample.

More specifically, a first object of the invention is to make it possible to increase the resolution of the sensitivity of the detection by NMR.

A second object of the invention is to implement the NMR analysis at lower cost.

A third object of the invention is an NMR solution which ensures the safety of the operatives and which is environmentally friendly.

To this end, the invention relies on an NMR analysis method for analysing a solid sample positioned in a sample-holder, characterized in that it comprises the following steps:
generation of a plurality of high-pressure gaseous flows from at least one first source of a high-pressure gas;
cooling of the gaseous flows in at least one heat exchanger from the circulation of a coolant originating from at least one second source;
rotation of the sample-holder by a first cooled high-pressure gaseous flow and cooling of the sample-holder by a second cooled high-pressure gaseous flow.

The NMR analysis method may comprise a step of adjustment of the speed of rotation of the sample-holder by variation of the pressure and/or the flow rate of the at least one first source of high-pressure gas.

The first high-pressure gaseous flow can drive the rotation of the sample-holder by its action on fins or blades of a device linked to the sample-holder to drive its rotation.

The first high-pressure gaseous flow can reach a flow rate so as to drive the rotation of the sample-holder at a rotation frequency greater than or equal to 20 kHz, or greater than or equal to 30 kHz.

The NMR analysis method can comprise a step of adjustment of the temperature of the high-pressure gaseous flows by the variation of the pressure and/or the flow rate of at least one second source of coolant gas.

The temperature of the high-pressure gaseous flows arriving at the probe comprising the sample-holder can be regulated to a temperature less than or equal to 10 K.

The temperature of the high-pressure gaseous flows arriving at the probe comprising the sample-holder can be adjustable within a range of 4.2 to 300 K inclusive.

The first high-pressure gaseous flow for rotating the sample-holder and the second high-pressure gaseous flow for cooling the sample-holder can exhibit temperatures that are substantially equal at the probe comprising the sample-holder.

The NMR analysis method can generate a third gaseous flow from the first source of a high-pressure gas to support the sample-holder.

The NMR analysis method can comprise a step of setting setpoints of temperature and rotation speed of the sample-holder, and can comprise a step of regulating the temperature and the flow rate of the high-pressure gaseous flows to these setpoints by modifying the pressure and/or the flow rate of the two gas sources.

The invention relates also to a computer program comprising code means suitable for implementing the steps of an NMR analysis method as described previously when the computer program is run on a computer.

The invention relates also to an NMR analysis device, comprising a sample-holder, suitable for receiving a solid sample to be analysed, and at least one first source of a high-pressure gas for generating gaseous flows intended to rotate and cool the sample-holder, characterized in that it comprises at least one second source of a coolant gas for cooling the high-pressure gaseous flows originating from the at least one first source in at least one heat exchanger with circulation of coolant.

The NMR analysis device can comprise a central unit which implements an NMR analysis method as described previously.

The at least one exchanger can be an exchanger with counter-current between the high-pressure gaseous flows and the at least one coolant gas.

The NMR analysis device can comprise at least fluid/fluid exchanger with counter-current comprising tubes for the circulation of the high-pressure gaseous flows inserted into a tube in which a coolant gas circulates with counter-current.

The NMR analysis device can comprise at least one exchanger for reheating the temperature of the gases leaving the device and/or can comprise a device for recovering the gases leaving the device.

The at least one first source of a high-pressure gas and/or the second source of a coolant gas can consist of a helium or nitrogen cylinder.

These objects, features and advantages of the present invention will be explained in detail in the following description of a particular embodiment, given as a nonlimiting example in relation to the attached figures in which:

FIG. 1 schematically represents an NMR device according to one embodiment of the invention.

FIG. 2 schematically represents a section of an exchanger of the embodiment of the invention.

FIG. 3 schematically represents a side view of the heat exchanges within an exchanger of the embodiment of the invention.

Figure 4:
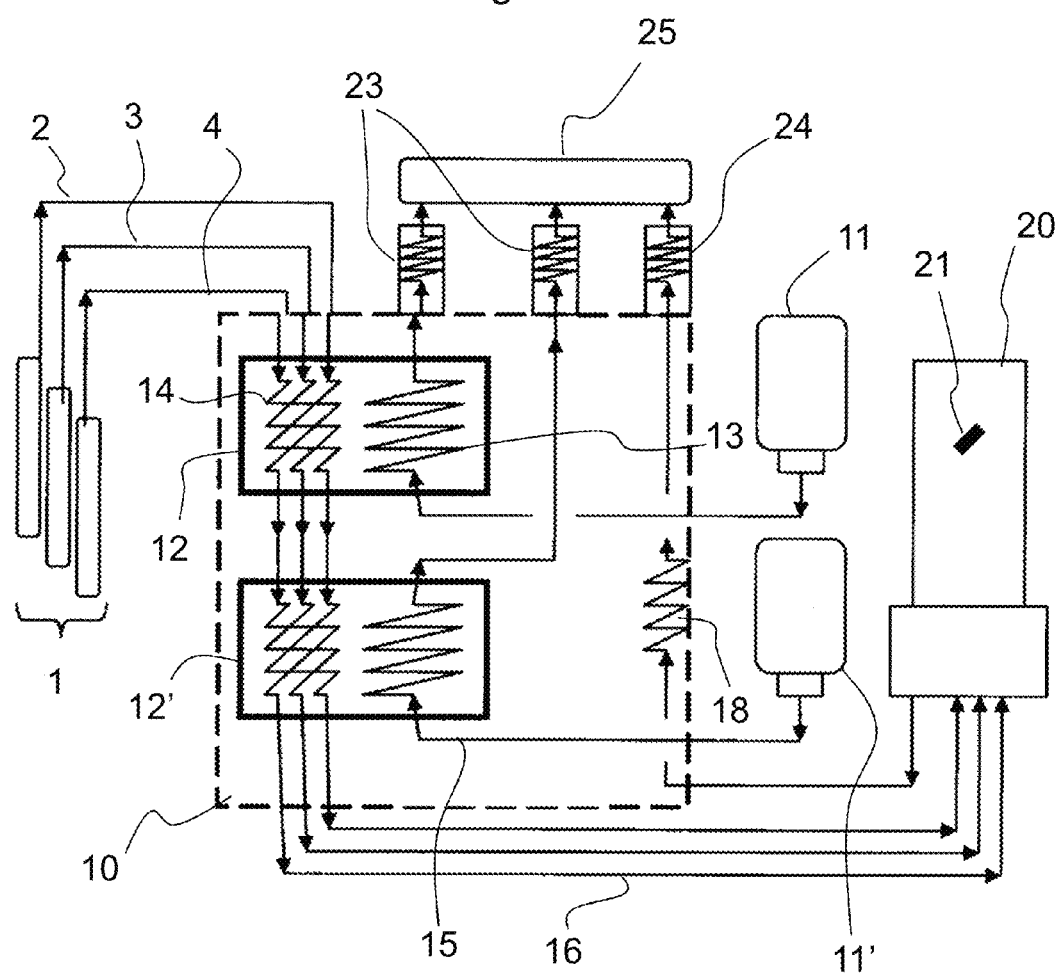

FIG. 4 schematically represents an NMR device according to a variant of the embodiment of the invention.

Figure 5:
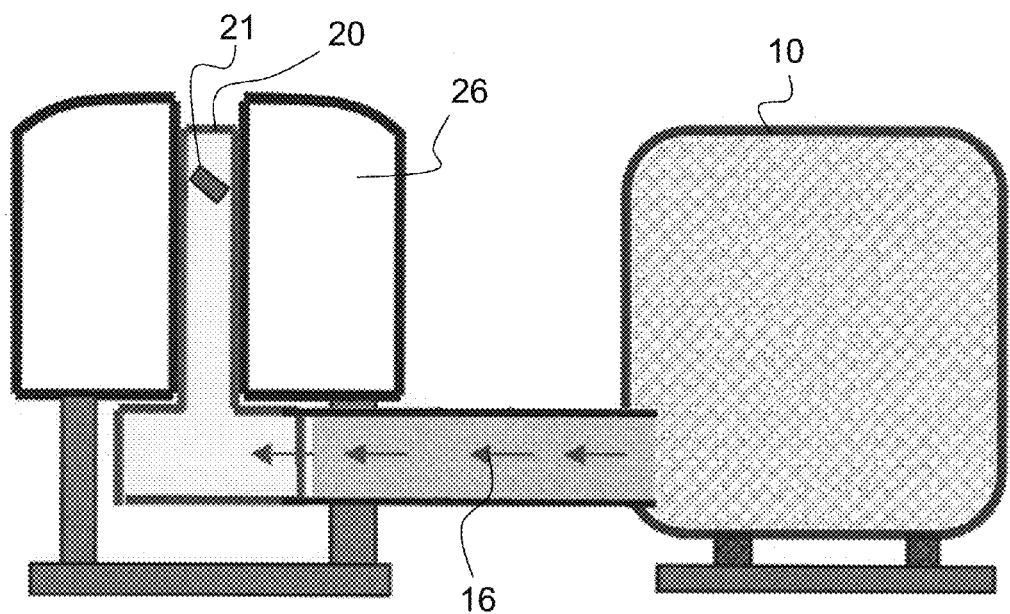

FIG. 5 schematically represents a side view of an NMR device according to the embodiment of the invention.

According to the approach retained, the embodiment of the invention proposes proceeding with the NMR detection from a temperature which can drop very low, to approximately 5 K for example, to achieve a high sensitivity. Reaching a very low temperature entails cooling the sample but also neutralizing the inevitable heat inputs at the probe from the frictions caused by the very rapid rotation of the sample-holder. In practice, it is also planned for the sample to be analysed to reach high rotation speeds, of the order of 30 kHz for example.

FIG. 1 represents the architecture of an NMR device according to an embodiment.

This device comprises at least one first high-pressure source 1 making it possible to generate three distinct high-pressure gaseous flows 2, 3, 4. As a variant, it is of course possible to use a plurality of sources each dedicated to one or more flows. This source 1 can, for example, consist of a cylinder of gas compressed to 200 bar and at room temperature. Its pressure is controlled by flow meters coupled to regulation valves. The high-pressure gas from this first source 1 can be nitrogen or helium. The three gaseous flows originating from this first source 1 pass through a cryostat 10, in which they are cooled in one or more heat exchangers 12, before reaching the NMR probe 20 comprising the sample-holder 21. The latter is positioned in an inclined manner with an angle that can be adjusted between the parallel and perpendicular axes of the static magnetic field. The radiofrequency components forming a transceiver, provided to receive in return a signal originating from the sample to be analysed, are also exposed to the cooling gaseous flow and subjected to the same temperature as the sample-holder 21. To be able to reach very low temperatures, the heat exchangers 12 are fed by a low-pressure cryogenic fluid, at low temperature lower than the temperature of the gas from the first source 1, which serves as coolant 15, originating from one or more second sources 11, distinct from the first high-pressure source 1. This coolant can also be nitrogen or helium.

FIGS. 2 and 3 more particularly represent a heat exchanger 12 of the cryostat 10 according to the embodiment of the invention. It comprises three high-pressure tubes 14 for the circulation in a first direction of, respectively, the three high-pressure gaseous flows 2, 3, 4. These three tubes are positioned inside a larger low-pressure tube 13 in which the coolant gas 15 circulates in a second, reverse direction. The tubes are formed from a material suited to cryogeny, for example made of a so-called low-carbon austenitic stainless steel grade. Thus, the heat exchanger 12 is of tubular fluid/fluid type with counter-current. It allows for a heat transfer between the two fluids, inducing a cooling of the high-pressure gaseous flows 2, 3, 4. This heat exchange between the two fluids is obtained by a forced convection between the gaseous flows 2, 3, 4 and the wall of their respective high-pressure tubes 14, then by conduction through this wall, before a new forced convection between the outer surface of this wall of the high-pressure tubes 14 and the coolant 15. The symmetrical distribution of the three high-pressure tubes 14 within the coolant flow guarantees the same output temperature for the three gaseous flows 2, 3, 4. At their ends, the tubes of this exchanger 12 can be equipped with a bellows, to facilitate their connections with the tubes of another exchanger or with the tubes outside the cryostat. These bellows also allow for an adaptation to the variations of the dimensions of the components of the device, such as the tubes, because of the significant temperature variations. The assembly is also spiral-wound to reduce the overall bulk of the exchanger 12. One or more exchangers 12, identical or not, can be arranged in series in the cryostat, in a modular fashion, to allow for the easy addition and removal of modules, depending on the needs. In the embodiment represented, two exchangers 12 are installed. Naturally, the cryostat can comprise any other number and any other type of heat exchanger than that described. However, the exchanger with coolant circulation allows for a dynamic treatment of the heat exchanges, to reach very low temperatures.

The cryostat 10 takes the form of a vacuum chamber sealed by a removable plate which allows access to its internal part. Inlet and outlet connectors are arranged on this plate, to allow for the passage of the abovementioned fluids and for data communication devices, for example from pressure, temperature, rotor frequency, electrical power and other such sensors. A dynamic vacuum of the order of $10^{-5}$ mbar is maintained in the vacuum chamber of the cryostat to minimize the thermal losses by gaseous convection and conduction. All the elements inside the cryostat are mechanically fixed by parts made of a material with very low thermal conductivity, which limits the thermal losses by thermal conduction. These components are, furthermore, protected from the ambient radiation emitted by the internal surface of the vacuum chamber, approximately at 300 K, by a thermal screen kept at low temperature by a circulation 18 of refrigerated fluid. This circulation is obtained by collecting, at the output of the NMR probe, all the gaseous flows 2, 3, 4 which have been used, which form an overall flow that is sufficiently powerful to bring the thermal screen of the cryostat to an intermediate temperature between the ambient temperature of the vacuum chamber and the coldest temperature of the cryostat. This arrangement makes it possible, furthermore, to optimize the use of the fluid originating from the first high-pressure source 1. The vacuum chamber is made of a weakly magnetic material, and its thermal screen is made of a metallic material with very good thermal conductivity. The insulation of the chamber can be obtained by a first coverage of a superinsulator, such as one based on MLI (multilayer insulation), while a second similar coverage directly covers the exchangers 12.

Then, at the output of the cryostat 10, the three gaseous flows 2, 3, 4 reach the NMR probe 20, advantageously cooled to the same temperature, and fulfil the three functions mentioned previously. As a variant, the temperatures may differ, but are preferentially equal to one another to within 100%. The first high-pressure flow 2 rotates the sample, the second high-pressure flow 3 cools the sample, and the third high-pressure flow 4 supports the sample-holder.

FIG. 4 represents a variant embodiment of the NMR device in which the two exchangers 12, 12' of the cryostat 10 are fed by two distinct sources 11, 11' of coolant gas. This solution makes it possible, for example, to use nitrogen as cold source for a first stage formed by the first exchanger 12, operating in the temperature range from 90 to 300 K, then helium as cold source for a second exchanger stage 12', covering the temperature range up to 5 K.

Naturally, other variants can be envisaged to generate one or more coolant flows and to cool the high-pressure gaseous flows. Also, three high-pressure gaseous flows 2, 3, 4 are used, but, as a variant, any other solution can be envisaged with at least the first two gaseous flows 2, 3 mentioned previously.

Finally, the NMR device according to the embodiment is equipped at the output with a fluid reheating and recovery system. The coolant gases are reheated in exchangers 23 at the output of the cryostat 10. Similarly, the high-pressure gaseous flows 2, 3, 4 are redirected at the output of the NMR probe to an exchanger 24. These exchangers 23, 24 provided at the output of the device make it possible to raise the temperature of the gases used by the device, preferably to room temperature, or to in the vicinity of room temperature. This reheating ensures the safety of personnel and avoids burns from contact with very cold parts, by avoiding falls from slips following the melting of the condensates, or electrocution. It also makes it possible to reduce the risks of degradation of the hardware by short-circuits or by oxidation of metal parts. Then, at least the most costly fluids, such as helium, can be recovered by a recovery device 25, to be reused.

FIG. 5 represents a side view of the NMR device according to the embodiment. A rigid cryogenic line 16 makes it possible to conduct the cooled high-pressure gaseous flows 2, 3, 4 from the output of the cryostat 10 to the NMR probe 20. This line is short, with a length of the order of a meter, insulated, pumped to a secondary vacuum and equipped with a thermal screen. The NMR probe 20 comprises a rotationally mobile sample-holder 21, placed in a device 26 to form the static NMR measurement magnetic field.

This solution finally presents the following advantages:
the flow rate of the gaseous flows 2, 3, 4 from the first high-pressure source is chosen by acting on the pressure on this first source, which ultimately makes it possible to choose the speed of rotation of the sample-holder which depends on this flow rate;
the temperature of the flows 2, 3, 4 is determined by at least one distinct and colder coolant originating from an independent source 11. The variation of the pressure of this independent source makes it possible to set the flow rate of the coolant gaseous flow and therefore ultimately choose the temperature of the gaseous flows 2, 3, 4 at the output of the cryostat 10.

This solution thus dissociates the function of cooling of the flows 2, 3, 4 arriving in the NMR probe from the function of high-pressure generation of these flows intended to cool the sample, to rotate the sample, and to support the sample, which is not the case in the prior art solutions. In this way, it is possible to choose the temperature according to a range of 300 to 4.2 K, independently of the speed of rotation of the sample, which can also be set at a value greater than or equal to 20 kHz, even 30 kHz.

Furthermore, the device comprises a central unit, not represented, which comprises at least one computer and hardware and software elements to implement the steps of the NMR detection method which will be detailed hereinbelow. This management unit comprises a human-machine interface which makes it possible to set sample-holder temperature and rotation speed setpoints. The device implements a step of regulation of the pressures of the high- and low-pressure gas sources 1, 11, to reach and observe these setpoint values. For this, it acts on actuators of the gas sources, by sending commands via communication devices. In return, it receives the values of these pressures, measured by sensors and transmitted by the communication devices.

The device in fact comprises a number of sensors making it possible to measure its operating conditions, and transmit the measured values to the central unit. For example, temperature probes based on Cernox™ resistors and platinum are used notably at the core of the cryostat, complementing pressure sensors, to follow the trend of the energy phenomena and make it possible to regulate the device.

The method for detecting and analysing by NMR a solid sample positioned in a sample-holder 21 of an NMR device as described above therefore comprises the following steps:
generation of a plurality of high-pressure gaseous flows 2, 3, 4 from a first source 1 of a high-pressure gas;
cooling of the gaseous flows in at least one heat exchanger 12 from a coolant gas 15 originating from a second source of gas, colder and preferably low-pressure;
rotation of the sample-holder by a first high-pressure gaseous flow and cooling of the sample-holder by a second high-pressure gaseous flow.

The NMR detection method comprises a step of adjustment of the speed of rotation of the sample-holder 21 by variation of the pressure of the first high-pressure gas source 1 and therefore the resulting flow rate of the first gaseous flow 2, intended to act on fins or blades linked to the sample-holder 21. This pressure is advantageously set at a sufficient level to reach a rotation speed greater than or equal to 20 kHz, or greater than or equal to 30 kHz, of the sample-holder. As a variant, the flow rate may be determined by a setting other than the pressure of the first source.

The NMR detection method further comprises a step of adjustment of the temperature of the high-pressure gaseous flows by the variation of the pressure and/or the flow rate of the second source of coolant gas. The latter is chosen to achieve a temperature of the high-pressure gaseous flows arriving at the sample-holder that is less than or equal to 10 K, being able to drop to 4.2 K inclusive, and/or be variable (notably adjustable) within a range of 4.2 to 300 K inclusive.

The invention claimed is:

1. NMR analysis method for analysing a solid sample positioned in a sample-holder, which comprises:
generating a plurality of high-pressure gaseous flows from at least one first source of a high-pressure gas;
cooling the gaseous flows in at least one heat exchanger with circulation of a coolant gas originating from at least one second source of gas;
rotating the sample-holder by a first gaseous flow which is a cooled high-pressure gaseous flow and cooling the sample-holder by a second gaseous flow which is a cooled high-pressure gaseous flow.

2. The NMR analysis method according to claim 1, comprising adjusting a speed of rotation of the sample-holder by varying at least one of (i) the pressure and (ii) a flow rate of the at least one first source of high-pressure gas.

3. The NMR analysis method according to claim 1, wherein the first gaseous flow drives the rotation of the sample-holder by acting on fins or blades of a device linked to the sample-holder to drive the rotation of the sample-holder.

4. The NMR analysis method according to claim 3, wherein the first gaseous flow reaches a flow rate so as to drive the rotation of the sample-holder at a rotation frequency greater than or equal to 20 kHz.

5. The NMR analysis method according to claim 1, comprising adjusting a temperature of the high-pressure gaseous flows by varying at least one of (i) a pressure of at least one second source of coolant gas and (ii) a flow rate of the at least one second source of coolant gas.

6. The NMR analysis method according to claim 5, wherein the temperature of the high-pressure gaseous flows arriving at a probe comprising the sample-holder is regulated to a temperature less than or equal to 10K.

7. The NMR analysis method according to claim 5, wherein the temperature of the high-pressure gaseous flows arriving at a probe comprising the sample-holder is adjustable within a range of 4.2 to 300 K inclusive.

8. The NMR analysis method according to claim 1, wherein the first high-pressure gaseous flow for rotating the sample-holder and the second high-pressure gaseous flow for cooling the sample-holder exhibit temperatures that are equal at a probe comprising the sample-holder.

9. The NMR analysis method according to claim 1, comprising generating a third gaseous flow from the first source of a high-pressure gas to support the sample-holder.

10. The NMR analysis method according to claim 1, comprising setting setpoints of temperature and rotation speed of the sample-holder and regulating the temperature and the flow rate of the high-pressure gaseous flows to the setpoints by modifying at least one of (i) the pressure and (ii) the flow rate of at least one of the first and second sources of gas.

11. Computer program comprising a code means suitable for implementing an NMR analysis method according to claim 1, when the computer program is run on a computer.

12. NMR analysis device comprising:
- a sample-holder, suitable for receiving a solid sample to be analysed,
- at least one first source of a gas which is a high-pressure gas for generating gaseous flows intended to rotate and cool the sample-holder,
- at least one heat exchanger,
- at least one second source of a gas which is a coolant gas for cooling the high-pressure gaseous flows originating from the at least one first source in the at least one heat exchanger with circulation of coolant, and
- a central unit which implements an NMR analysis method according to claim 1.

13. The NMR analysis method according to claim 2, wherein the first gaseous flow drives the rotation of the sample-holder by acting on fins or blades of a device linked to the sample-holder to drive the rotation of the sample-holder.

14. The NMR analysis method according to claim 13, wherein the first gaseous flow reaches a flow rate so as to drive the rotation of the sample-holder at a rotation frequency greater than or equal to 20 kHz.

15. The NMR analysis method according to claim 2, comprising adjusting a temperature of the first gaseous flows by varying at least one of the pressure and the flow rate of the at least one second source of gas.

16. NMR analysis device, comprising:
- a sample-holder, suitable for receiving a solid sample to be analysed,
- at least one first source of a gas which is a high-pressure gas for generating gaseous flows intended to rotate and cool the sample-holder,
- at least one heat exchanger,
- at least one second source of a gas which is a coolant gas for cooling the high-pressure gaseous flows originating from the at least one first source in the at least one heat exchanger with circulation of coolant.

17. The NMR analysis device according to claim 16, wherein the at least one exchanger is an exchanger with counter-current between the high-pressure gaseous flows and the at least one coolant gas.

18. The NMR analysis device according to claim 16, comprising at least one fluid/fluid exchanger with counter-current comprising tubes for the circulation of the high-pressure gaseous flows inserted into a tube in which a coolant gas circulates with counter-current.

19. The NMR analysis device according to claim 16, comprising at least one of (i) at least one exchanger for reheating a temperature of the gases leaving the device, and (ii) a device for recovering the gases leaving the device.

20. The NMR analysis device according to claim 16, wherein at least one of (i) the at least one first source of a gas which is a high-pressure gas, and (ii) the second source of a gas which is a coolant gas consists of a helium or nitrogen cylinder.

* * * * *